(12) United States Patent
Franke et al.

(10) Patent No.: US 9,504,851 B2
(45) Date of Patent: Nov. 29, 2016

(54) MAGNETIC RESONANCE IMAGING OF BONE TISSUE

(75) Inventors: Jochen Frederik Franke, Rheinstetten (DE); Michael Adam Meltsner, Fitchburg, WI (US); Volkmar Schulz, Wuerselen (DE); Melanie Suzanne Kotys, Shaker Heights, OH (US); Lizette Warner, Wickliffe, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 89 days.

(21) Appl. No.: 14/126,979

(22) PCT Filed: Jun. 18, 2012

(86) PCT No.: PCT/IB2012/053050
§ 371 (c)(1),
(2), (4) Date: Mar. 27, 2014

(87) PCT Pub. No.: WO2012/001399
PCT Pub. Date: Jan. 3, 2013

(65) Prior Publication Data
US 2014/0221816 A1    Aug. 7, 2014

Related U.S. Application Data

(60) Provisional application No. 61/636,103, filed on Apr. 20, 2012.

(30) Foreign Application Priority Data

Jun. 27, 2011  (EP) ..................................... 11171444

(51) Int. Cl.
*A61N 5/10*  (2006.01)
*G01R 33/48*  (2006.01)
(Continued)

(52) U.S. Cl.
CPC ........... *A61N 5/1039* (2013.01); *A61B 6/4417* (2013.01); *A61B 8/0875* (2013.01);
(Continued)

(58) Field of Classification Search
None
See application file for complete search history.

(56) References Cited

U.S. PATENT DOCUMENTS 5,909,119 A    6/1999  Zhang
6,037,772 A *  3/2000  Karczmar .......... G01R 33/4833
                                                    324/309
(Continued)

FOREIGN PATENT DOCUMENTS

EP    2221627 A1    8/2010

OTHER PUBLICATIONS

Krug, "High-resolution Imaging Techniques for the Assessment of Osteoporosis", Radiol Clin North Am. 48(3), 601-621, 2010.*
(Continued)

*Primary Examiner* — Tse Chen
*Assistant Examiner* — Joanne Hoffman

(57) ABSTRACT

A medical apparatus includes a magnetic resonance imaging system for acquiring magnetic resonance data from an imaging volume, a processor for controlling the medical apparatus, and a memory containing machine executable instructions and a pulse sequence. The magnetic resonance data acquired using the pulse sequence comprises free induction decay data and multiple gradient echo data. Execution of the instructions causes the processor to acquire the magnetic resonance data using the magnetic resonance imaging system in accordance with the pulse sequence, and reconstruct an in-phase image, a fat-saturated image, a water-saturated image, and an ultra-short echo time image from the magnetic resonance data, wherein the ultra-short echo time image comprises bone image data.

18 Claims, 10 Drawing Sheets

(51) Int. Cl.
G01R 33/56 (2006.01)
G01R 33/561 (2006.01)
A61B 8/08 (2006.01)
A61B 6/00 (2006.01)
A61B 6/03 (2006.01)

(52) U.S. Cl.
CPC ....... *G01R33/4816* (2013.01); *G01R 33/4828* (2013.01); *G01R 33/5608* (2013.01); *G01R 33/5616* (2013.01); *A61B 6/037* (2013.01); *A61B 8/5261* (2013.01); *A61N 2005/1052* (2013.01); *A61N 2005/1055* (2013.01); *A61N 2005/1062* (2013.01); *G01R 33/481* (2013.01); *G01R 33/4808* (2013.01)

(56) References Cited

U.S. PATENT DOCUMENTS

| | | | |
|---|---|---|---|
| 6,263,228 B1 | 7/2001 | Zhang | |
| 6,459,922 B1 | 10/2002 | Zhang | |
| 7,602,184 B2* | 10/2009 | Du | 324/307 |
| 8,744,154 B2 | 6/2014 | Van Den Brink | |
| 2002/0087274 A1* | 7/2002 | Alexander | A61B 5/1114 702/19 |
| 2003/0219098 A1* | 11/2003 | McNutt et al. | 378/65 |
| 2006/0058634 A1* | 3/2006 | Ikezaki | G01R 33/4828 600/410 |
| 2007/0041499 A1* | 2/2007 | Lu et al. | 378/65 |
| 2008/0310590 A1* | 12/2008 | Meyer | A61N 5/103 378/65 |
| 2009/0009167 A1 | 1/2009 | Du | |
| 2010/0204563 A1* | 8/2010 | Stodilka et al. | 600/411 |
| 2011/0261180 A1* | 10/2011 | Simon | A61B 19/5244 348/77 |
| 2011/0282473 A1* | 11/2011 | Pavlovskaia et al. | 700/98 |

OTHER PUBLICATIONS

Du, "Qualitative and quantitative ultrashort-TE MRI of cortical bone", NMR Biomed. 26(5), 489-506, published online 2012.*
Du, "Qualitative and quantitative ultrashort echo time (UTE) imaging of cortical bone", Journals of Magnetic Resonance 207 304-311, 2010.*
Disler, "In-Phase and Out-of-Phase MR Imaging of Bone Marrow: Prediction of Neoplasia Based on the Detection of Coexistent Fat and Water", AJR, 169, 1439-1447, 1997.*
Johansson, Adam et al "CT Substitute Derived from MRI Sequences with Ultrashort Echo Time", Medical Physics, vol. 38, No. 5, May 2011, pp. 2708-2714.
Rahmer, J. et al "Merging UTE Imaging, Water-Fat Separation, and T2 Mapping in a Single 3D MSK Scan", Proceedings of the International Society Magnetic Resonance Medicine, vol. 18, 2010, p. 3224.
Bharath, Krishnan et al "Simultaneous PET/MR Hybrid Imaging: MR Based Continuous Valued Attenuation Map Generation and its effect on Quantitative PET Imaging", Proceedings of the International Society Magnetic Resonance Medicine, vol. 20, 2012, pp. 2717.

Wu, Yaotang, et al "Density of Organic Matrix of native Mineralized Bone Measured by Water and Fat Suppressed Proton Projection MRI", Magnetic Resonance in Medicine, vol. 50, 2003, pp. 59-68.
Robson, Matthew D. et al "Magnetic Resonance: An Introduction to Ultrashort TE (UTE) Imaging", Journal of Computer Assisted Tomography, vol. 27, No. 6, 2003, pp. 825-846.
Rahmer, J. et al "Selective 3D Ultrashort Te Imaging: Comparison of "Dual-Echo" Acquisition and Magnetization Preparation for Improving Short-T2 Contrast", Magnetic Resonance Materials in Physics, vol. 20, No. 2, 2007, pp. 83-92.
Keereman, Vincent et al "MR-Based Attenuation Correction for PET using an Ultrashort ECHO Time (UTE) Sequence", 2008 IEEE Nuclear Science Symposium Conference Record, pp. 4656-4661.
Brodsky, Ethan K. et al "Generalized k-Space Decomposition with Chemical Shift Correction for Non-Cartesian Water_fat Imaging", Magnetic Resonance in Medicine, vol. 59, 2003, pp. 1151-1164.
Hofmann, Matthias et al "Towards Quantitative PET/MRI: A Review of MR-based Attenuation Correction Techniques", European Journal of Nuclear Medicine and Molecular Imaging, vol. 36, No. 1, 2008, pp. 93-104.
Berker, Yannick et al "MRI-Based Attenuation Correction for Hybrid PET/MRI Systems: A 4-Class Tissue Segmentation Technique using a Combined Ultrashort-Echo-Time/Dixon MRI Sequence", The Journal of Nuclear Medicine, vol. 53, No. 5, May 2012, pp. 796-804.
Du, Jiang et al "Orientational Analysis of the Achilles Tendon and Enthesis using an Ultrashort Echo Time Spectroscopic Imaging Sequence", Magnetic Resonance Imaging, vol. 28, 2010, pp. 178-184.
Wang, Kang et al "k-Space Water-Fat Decomposition with T2 Estimation and Multifrequency Fat Spectrum Modeling for Ultrashort Echo Time Imaging", Journal of Magnetic Resonance Imaging, vol. 31, 2010, pp. 1027-1034.
Van Der Kouwe, A.J. et al "Fluster: A Combined Multiecho Radia/Cartesian Encoded Gradient Echo Sequence for Bone and Soft Tissue Segmentation", Proceedings of the International Society Magnetic Resonance Medicine, vol. 17, 2009, p. 2685.
Keereman, V. et al "Estimation of Attenuation Maps from UTE Derived R2 Images", Proceedings of the International Society Magnetic Resonance Medicine, vol. 17, 2009, pp. 2774-2775.
Yu, Huanzhou et al "Multiecho Reconstruction for Simultaneous Water-Fat Decomposition and T2 Estimation", Journal of Magnetic Resonance Imaging, vol. 26, 2007, pp. 1153-1161.
Reichert, Ines L.H. et al "Magnetic Resonance Imaging of Cortical Bone with Ultrashort TE Pulse Sequences", Magnetic Resonance Imaging, vol. 23, 2005, pp. 611-618.
Wang, K. et al "Water/Fat Separation of Short T2 Tissue using Multi-echo Ultra-Short Echo Time (UTE) Imaging and IDEAL", Proceedings of the International Society Magnetic Resonance Medicine, 2010.
Franke et al Utile "A Fast Combined UTE-DIXON Four Class Attenuation Correction Technique for PET/MR" Proc. Intl. Soc. Mag. Reson. Med. 19, 2011, p. 4581.
J. Ellermann et al "The Ultrastructure of Bone using Selective Saturation in Swift at 9.4 T" Proc. Intl. Soc. Mag. Res. Med. 17, 2009 p. 849.

* cited by examiner

MAGNETIC RESONANCE IMAGING OF BONE TISSUE

CROSS-REFERENCE TO PRIOR APPLICATIONS

This application is the U.S. National Phase application under 35 U.S.C. §371 of International Application No. PCT/IB2012/053050, filed on Jun. 18, 2012, which claims the benefit of European Patent Application No. 11171444.0, filed on Jun. 27, 2011 and U.S. Provisional Patent Application No. 61/636,102, filed on Apr. 20, 2012. These applications are hereby incorporated by reference herein.

FIELD

The invention relates to magnetic resonance imaging, in particular to the use of magnetic resonance imaging for radiation therapy planning.

BACKGROUND

Magnetic Resonance (MR) images that can separate tissue, bone, and air are beneficial for all applications where MR is used in combination with irradiating imaging techniques, such as Positron Emission Tomography (PET) and Single Photon Emission Computed Tomography (SPECT), and with planning for irradiating therapy techniques, such as Magnetic Resonance-Radio Therapy simulation. Unlike Hounsfield units used in CT, there is no simple relation between the MR image intensity and tissue density. For instance, using conventional MR sequences, cortical bone and air filled cavities both show no signal intensity whereas their densities are substantially different. Ultimately the ability to reliably identify additional tissue types in an MR image while the MR-acquisition time should be kept at a minimum would be beneficial.

SUMMARY

Embodiments of the invention may provide for a means of identifying different tissue types within a subject using magnetic resonance imaging. Embodiments may achieve this by using a pulse sequence which comprises commands to acquire free induction decay data and multiple gradient echoes. The free induction decay data is acquired on a timescale of several milliseconds. This enables the acquisition of free induction decay data from bone tissue. Data from multiple gradient echoes is also acquired. The commendation of acquiring the free induction decay data and the multiple gradient echo data allows a variety of images to be constructed: an in-phase image, a fat-such saturated image, a water-saturated image, and an ultra-short echo time image. Using a pulse sequence which may be used to reconstruct such different images may be beneficial because all of the image data necessary for radiation therapy planning and/or reconstructing images from radio-isotope imaging systems is provided. Using such a pulse sequence may also be beneficial because it may reduce the time necessary to acquire the images.

An embodiment of the invention may provide for a pulse sequence for magnetic resonance imaging which combines the features of an ultra-short echo time (UTE) pulse sequence with a DIXON acquisition. For example the pulse sequence may be a UTE triple-echo (UTILE) MR-sequence combining the UTE and DIXON acquisition in a single acquisition. This example may be implemented using a pulse sequence that samples fast induced decay (FID) at short echo times, at time TE1, followed by two gradient echoes, at times TE2 and TE3. The echo times TE2 and TE3 may be optionally adjusted to where water and fat are almost opposed- and in-phase, respectively.

Cortical bone may be segmented from the calculated relative difference between the magnitude information of echo one (M1) and echo three (M3) by an empirically determined global threshold after masking out air areas, potentially by thresholding. Soft tissue and adipose tissue decomposition may be achieved by applying a three point Dixon signal modeling technique using the magnitude and the unwrapped phase information of all three echoes. This single acquisition may provide up to 5 sets of images:

1. images of bone
2. water-only images (i.e., fat-saturated images)
3. fat-only images (i.e., water-saturated images)
4. in-phase images
5. opposed-phase images A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer-readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. The memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Radio-isotope imaging data is defined herein as two or three dimensional data that has been acquired using a medical imaging scanner that is configured to detect the radioactive decay of radioisotopes. A radio-isotope imaging system is defined herein as a apparatus adapted for acquiring information about the physical structure of a patient and construct sets of two dimensional or three dimensional medical image data by detecting radiation emitted by radioactive markers or traces within the patient. Radio-isotope imaging data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical apparatus comprising a magnetic resonance imaging system for acquiring magnetic resonance data from an imaging volume. The medical apparatus further comprises a processor for controlling the medical apparatus. The processor may be replaced by a controller or a control system. The medical apparatus further comprises a memory containing machine executable instructions and a pulse sequence. The machine executable instructions may cause the processor to control the magnetic resonance imaging system. A pulse sequence as used herein is encompassed by a set of instructions or operations performed as a function of time which together may be used to control or to generate commands for controlling the magnetic resonance imaging system to acquire the magnetic resonance data. The pulse sequence may be in a machine executable form or it may be in a graphical form which is adapted for manipulation or change by a human operator on a graphical user interface. If in graphical form the pulse sequence may be converted into a machine executable form by a suitable program or program module.

The magnetic resonance data acquired using the pulse sequence comprises free induction decay data and multiple gradient echo data. Free induction decay data as used herein encompasses a measurement of the free induction decay curve measured during the acquisition of the magnetic resonance data. The free induction decay data may for instance be free induction decay which decays in a characteristic time constant T2 or T2*. An echo signal is a signal which is generated from a free induction decay using a bipolar switched magnetic gradient. There is an echo which is produced when the magnetic field gradient is reversed. Gradient echo data as used herein encompasses the measurement recording of such an echo signal. Multiple gradient echo data as used herein encompasses the recording of multiple echo signals.

Execution of the instructions causes the processor to acquire the magnetic resonance data using the magnetic resonance imaging system in accordance with the pulse sequence. This is to say that the pulse sequence commands or control sequences were used to control the magnetic resonance imaging system to acquire the magnetic resonance data. Execution of the instructions cause the processor to reconstruct an in-phase image, a fat-saturated image, a water-saturated image, and an ultra-short echo time image from the magnetic resonance data. The ultra-short echo time image comprises bone image data. An in-phase image as used herein encompasses an image reconstructed from magnetic resonance data that comprises the T1 and regular proton weighted image.

A fat-saturated image as used herein encompasses an image where the fat protons were saturated prior to image acquisition so that only a small nuclear magnetic resonance signal results from the fat protons. A fat-saturated image is typically used to show the concentration or location of water protons with the fat protons removed. Likewise a water-saturated image as used herein encompasses an image reconstructed from magnetic resonance data where water protons were saturated prior to the acquisition of data such that the water protons or hydrogen protons produces a small nuclear magnetic resonance signal. A water-saturated image is typically used for showing the location of fat or adipose tissue. An ultra-short echo time image as used herein encompasses an image reconstructed from a free induction decay data where the free induction decay occurred on an extremely short timescale. The free induction decay may have a time constant on the order of several milliseconds. The ultra-short echo time enables the imaging of tissue with extremely small free induction decay values such as tendons or bone. Bone image data as used herein encompasses magnetic resonance data which contains free induction decay data which is descriptive of the position and location of bone within the subject.

This embodiment may have the advantage that the in-phase image, the fat-saturated image, the water-saturated image, and the ultra-short echo time image were acquired using a single pulse sequence. This may mean that all of these images have the same positional relationship and are able to be used for more accurately reconstructing the geometric structure or internal anatomy of a subject. Further since all these images are acquired at the same time the acquisition time is reduced.

The reconstruction of the in-phase image, the fat-saturated image, the water-saturated image and the ultra-short echo time image may for instance be reconstructed using a Dixon method. For instance the images may be reconstructed using a two-point Dixon method.

In another embodiment execution of the instructions further cause the processor to construct a medullary bone image from the water-saturated image. In some embodiments fat that is imaged in the water-saturated image may be removed from the medullary bone image by a suitable anatomical model. For instance a deformable shape model may be fit to the medullary bone identified in the medullary bone image and used to remove fat or adipose tissue. Execution of the instructions further causes the processor to construct a cortical bone image by subtracting the in-phase image from the ultra-short echo time image. Medullary bone as used herein refers to an image showing the location of medullary bone. Medullary bone is synonymous with trabecular or cancellous bone. Cortical bone is the hard outer layer of a bone and may also be referred to as compact bone tissue. Execution of the instructions further causes the processor to construct a complete bone image by adding the medullary bone image to the cortical bone image. This embodiment of the invention may have the advantage that the magnetic resonance imaging system was used for constructing an image of the bone tissue within a subject. This may be used for studying the bone tissue or it may be used in therapy planning.

In another embodiment execution of the instructions cause the processor to calculate a spatially dependent radiation attenuation coefficient using the complete bone image, the fat-saturated image, the in-phase image, and the ultra-short echo time image. For instance the ultra-short echo time image may be used to identify the location of bone and air pockets, for instance the ultra-short echo time phase may be used to identify the location of air pockets such as the sinuses of a subject. The complete bone image may contain information about varying bone density. The cortical and medullary bone have different densities. Using the information about the varying bone density in the calculation of the spatially dependent radiation attenuation coefficient may allow the spatially dependent radiation attenuation coefficient to be determined more accurately.

This embodiment may also have the advantage that the various types of images which are acquired or constructed may be used to accurately calculate a spatially dependent radiation attenuation coefficient. The spatially dependent radiation attenuation coefficient may for instance be used for either radiation therapy planning or in diagnostic radiology where the absorption of radiation needs to be accurately predicted for imaging such as positron emission tomography. These images allow the identification of different types of tissues or regions within the body. This anatomical information may be used to accurately model the absorption of radiation by different portions of the subject. In particular the in-phase image may be used for fitting segmentation models to the images. This may be extremely beneficial in further refining the calculation of the spatially dependent radiation attenuation coefficient.

In another embodiment the ultra-short echo time image is used for differentiating bone and air. The in-phase image is used for image segmentation. The fat-saturated image is also used for image segmentation.

Execution of the instructions further causes the processor to display the fat-saturated image, the in-phase image, the complete bone image, and the ultra-short echo time image on a graphical user interface. Execution of the instructions further causes the processor to receive radiation therapy planning data from the graphical user interface. In some embodiments the spatially dependent radiation coefficient is used along with input from the graphical user interface to calculate the radiation therapy planning data. This embodiment may be particularly beneficial because the data necessary for an operator or a physician to plan a radiation session or therapy is displayed on the graphical user interface. The user or operator may study the images and then use a mouse or other human input device to manipulate shapes and controls on the graphical user interface. The user's entry may then be translated into the radiation therapy planning data. This embodiment may be particularly beneficial because the data necessary for performing the radiation therapy has been presented and acquired all at the same time. This may result in an increase in the speed in which radiation therapy planning can be performed.

In another embodiment execution of the instructions further causes the processor to generate radiation therapy planning data using the fat-saturated image, the in-phase image, and the ultra-short echo time image, the complete bone image, the spatially dependent radiation coefficient, and a treatment plan using a radiation therapy planning program module. A treatment plan as used herein encompasses a data file descriptive of a plan for performing a radiation therapy. For instance the treatment plan may contain anatomical data descriptive of the patient or subject in conjunction with regions of the subject to be treated. The radiation therapy planning program module may contain executable code which is able to interpret the treatment plan and register it to at least one of the fat-saturated image, the in-phase image, and the ultra-short echo time image. This embodiment may have the advantage that the medical apparatus is able to acquire the magnetic resonance data and then proceed with planning and executing a radiation therapy on the patient or subject.

In another embodiment the medical apparatus further comprises a radiation therapy system. Execution of the instructions further causes the processor to generate radiation therapy control commands using the radiation therapy planning data. Execution of the instructions further causes the processor to treat the subject with the radiation therapy system by executing the radiation therapy control commands. The radiation therapy control commands as used herein encompass machine executable commands which control a radiation therapy system.

In another embodiment the radiation therapy system is a linear accelerator.

In another embodiment the radiation therapy system is a gamma knife.

In another embodiment the radiation therapy system is a charged particle therapy system. A charged particle therapy system as used herein is a system which is adapted for shooting charged particles such as charged nuclei or molecules at a target region of the subject. For example carbon nuclei or protons may be directed at a target zone of the subject.

In another embodiment the radiation therapy system is a proton therapy system. A proton therapy system as used herein is a therapy system which is adapted for shooting proton such as hydrogen nuclei at a target zone of the subject.

In another embodiment the radiation therapy system is an x-ray therapy system. An x-ray therapy system as used herein encompasses a system for directing x-rays in a target zone of a subject for performing radiation therapy.

In another embodiment the radiation therapy system is an external beam radiation system. An external beam radiation system as used herein encompasses a radiation therapy system for directing an external radiation beam at a target zone of a subject.

In another embodiment the radiation therapy system is a brachytherapy system.

In another embodiment execution of the instructions further causes the processor to receive radio-isotope imaging data. Radio-isotope imaging data as used herein encompasses data generated by the detection of radioactive decay of an isotope. The radio-isotope imaging data is generated in diagnostic imaging of a subject or patient.

Execution of the instructions further causes the processor to calculate a medical image using the radio-isotope image data and the spatially dependent radiation attenuation coefficient. The radio-isotope imaging data is generated by recording the detected radio-isotope decays within a subject. Knowing the spatially dependent radiation attenuation coefficient allows a more accurate determination of the location of the radio-isotope. The attenuation of the detected radiation can be better predicted by using knowledge of how this radiation is attenuated within the subject.

In another embodiment the medical apparatus further comprises a radio-isotope imaging system for acquiring the radio-isotope imaging data.

In another embodiment execution of the instructions further causes the processor to acquire the radio-isotope imaging data using the radio-isotope imaging system.

In another embodiment the radio-isotope imaging system is a positron emission tomography system.

In another embodiment the radio-isotope imaging system is a single photon emission computer tomography system.

In another embodiment execution of the instructions further causes the processor to reconstruct an opposed phase image from the magnetic resonance data. An opposed phase image as used herein encompasses an image with a signal from two distinct components such as fat and water signals are 180 degrees out of phase which causes the destructive interference of the nuclear magnetic resonance signal within a particular voxel. This embodiment may be beneficial when performing radiation therapy planning on particular types of tissue. For instance it may be beneficial in identifying lesions in the liver or the adrenal glands. It may also be beneficial for identifying the various pathological regions in the brain. The opposed phase image may for instance be displayed on the graphical user interface during the radiation therapy planning or it may for instance be used as an input for the radiation therapy planning program module.

In another embodiment execution of the instructions further causes the processor to reconstruct multiple echo images. An echo image is an image reconstructed from the recorded magnetic resonance data of a gradient echo. Multiple echo images are multiple images each reconstructed from the magnetic resonance data of multiple gradient echoes. the in-phase image, the fat-saturated image, the water-saturated image, and the ultra-short echo time image are constructed from the magnetic resonance data using a Dixon signal model. For instance the Dixon signal model may be a two-point Dixon signal model, a three-point Dixon signal model, or a four-point Dixon signal model. This embodiment may be advantageous because this provides for an effective and accurate means of constructing these images. The three-point Dixon signal model may be used in some embodiments to reconstruct the opposed phase image from the magnetic resonance data at the same time that the other images are also reconstructed.

In another aspect the invention provides for a method of operating a medical apparatus. The medical apparatus comprises a magnetic resonance imaging system for acquiring magnetic resonance data from an imaging volume. The method comprises the step of acquiring the magnetic resonance data using the magnetic resonance imaging system. The magnetic resonance data acquired comprises free induction decay data and multiple gradient echo data. The method further comprises the step of reconstructing an in-phase image, a fat-saturated image, a water-saturated image and an ultra-short echo time image from the magnetic resonance data. The ultra-short echo time image comprises bone image data.

In another embodiment the method further comprises the step of constructing a medullary bone image from the water-saturated image. The method further comprises the step of constructing a cortical bone image by subtracting the in-phase image from the ultra-short echo time image. The method further comprises the step of constructing a complete bone image by adding the medullary bone image to the cortical bone image.

In another embodiment the method further comprises the step of calculating a spatially dependent radiation attenuation coefficient using the complete bone image, the fat-saturated image, the in-phase image, and the ultra-short echo time image.

In another embodiment the ultra-short echo time image is used for differentiating bone and air. The in-phase image is used for image segmentation. The fat-saturated image is also used for image segmentation.

In another aspect the invention provides for a tangible computer-readable storage medium containing machine readable instructions for execution by a processor controlling a medical apparatus. The medical apparatus comprises a magnetic resonance imaging system for acquiring magnetic resonance data from an imaging volume. The computer-readable storage medium further contains a pulse sequence for controlling the magnetic resonance imaging system. The magnetic resonance data acquired using the pulse sequence comprises free induction decay data and multiple gradient echo data. Execution of the instructions causes the processor to acquire the magnetic resonance data using the magnetic resonance imaging system. Execution of the instructions further causes the processor to reconstruct an in-phase image, a fat-saturated image, a water-saturated image and an ultra-short echo time image from the magnetic resonance data. The ultra-short echo time image comprises bone image data.

In another embodiment execution of the instructions further causes the processor to construct a medullary bone image from the water-saturated image. Execution of the instructions further causes the processor to construct a cortical bone image by subtracting the in-phase image from the ultra-short echo time image. Execution of the instructions further causes the processor to construct a complete bone image by adding the medullary bone image to the cortical bone image.

In another aspect the invention provides for a controller for a medical apparatus. A controller as used herein encompasses an electronic apparatus adapted for controlling other systems or apparatuses. Since a processor or microcontroller are two non-limiting examples of a controller. The medical apparatus comprises a magnetic resonance imaging system for acquiring magnetic resonance data from an imaging volume. The controller is arranged to acquire the magnetic resonance data using the magnetic resonance imaging system. The controller is arranged to use a pulse sequence to control the operation of the magnetic resonance imaging system during acquisition of the magnetic resonance data. The magnetic resonance data acquired using the pulse sequence comprises free induction decay data and multiple gradient echo data. The controller is further arranged to reconstruct an in-phase image, a fat-saturated image, a water-saturated image, and an ultra-short echo time image from the magnetic resonance data. The ultra-short echo time image comprises bone image data.

In another embodiment the controller is further arranged to construct a medullary bone image from the water-saturated image. The controller is further arranged to construct a cortical bone image by subtracting the in-phase image from the ultra-short echo time image. The controller is further arranged to construct a complete bone image by adding the medullary bone image to the cortical bone image.

BRIEF DESCRIPTION OF THE DRAWINGS

In the following preferred embodiments of the invention will be described, by way of example only, and with reference to the drawings in which.

DETAILED DESCRIPTION

Like numbered elements in these figures are either equivalent elements or perform the same function. Elements which have been discussed previously will not necessarily be discussed in later figures if the function is equivalent.

Figure 1:
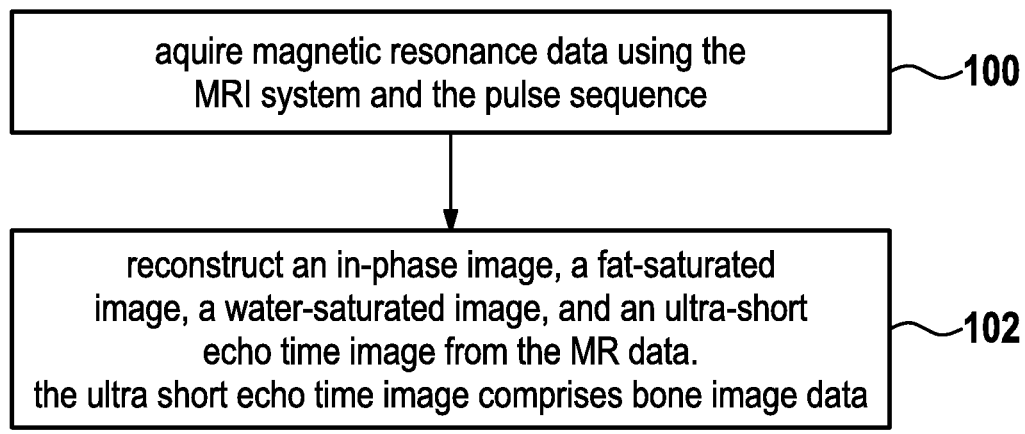
FIG. 1 shows flow chart which illustrates a method according to an embodiment of the invention.

FIG. 1 shows a flow diagram which illustrates a method according to an embodiment of the invention. In step 100 magnetic resonance data is acquired using an MRI system and a pulse sequence. The pulse sequence may for instance be a pulse sequence as is demonstrated in FIG. 3. Next in step 102 an in-phase image, a fat-saturated image, a water-saturated image, and an ultra-short echo time image may be reconstructed from the magnetic resonance data. The ultra-short echo time image comprises bone image data.

Figure 2:
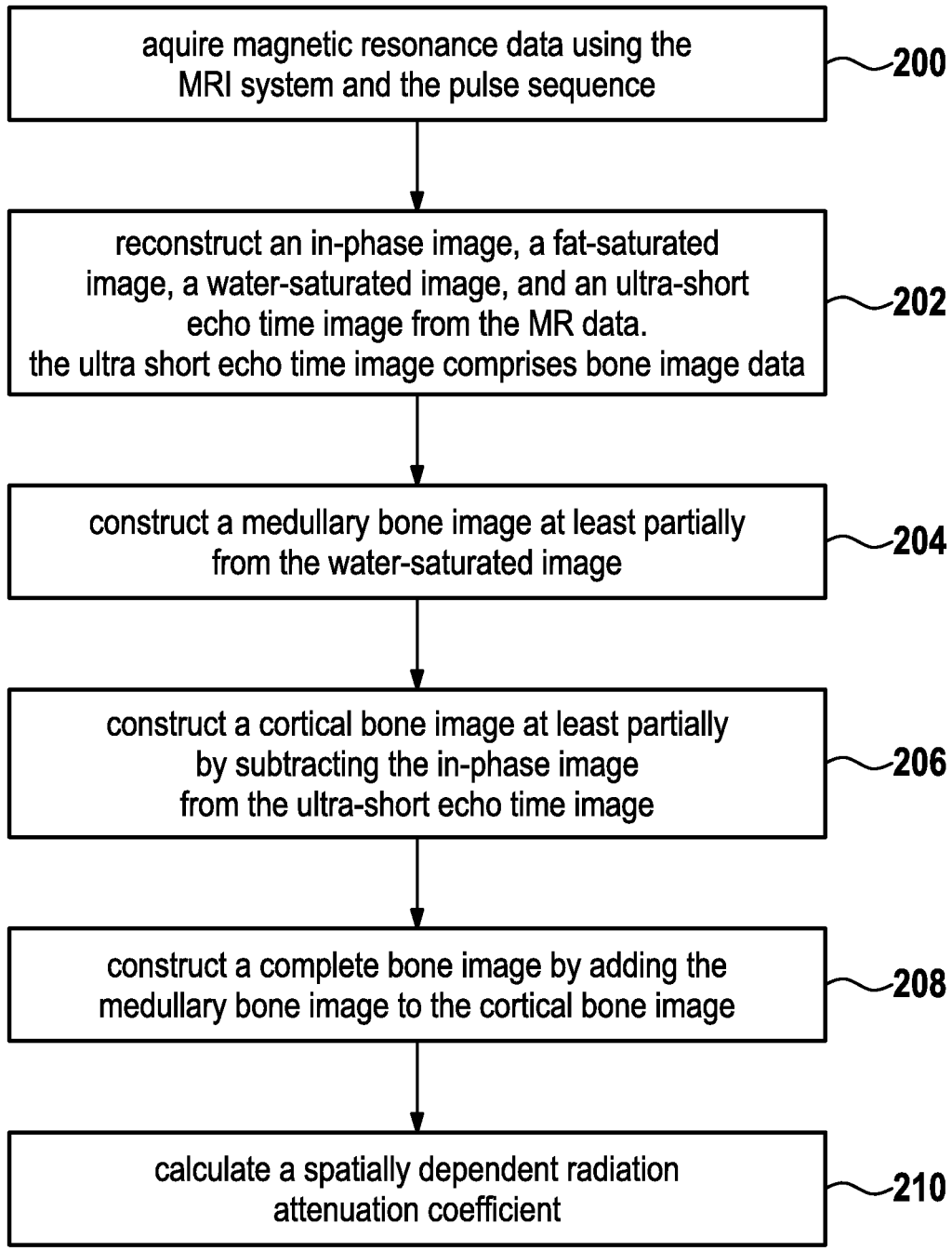
FIG. 2 shows flow chart which illustrates a method according to a further embodiment of the invention.

FIG. 2 shows a block diagram which illustrates a further embodiment of the method. In step 200 magnetic resonance data is acquired using the MRI system and a pulse sequence. In step 202 an in-phase image, a fat-saturated image, a water-saturated image, and an ultra-short echo time image are reconstructed from the magnetic resonance imaging data. The ultra-short echo time image comprises bone image data. A bone image data is image data which is descriptive of the anatomy of bone tissue within a patient or a subject. In step 204 a medullary bone image is constructed from the water-saturated image. In some embodiments this step may consist of removing information from the image using a model, for instance removing adipose tissue from the image. Next in step 206 a cortical bone image is constructed by subtracting the in-phase image from the ultra-short echo time image. Next in step 208 a complete bone image is constructed by adding the medullary bone image to the cortical bone image. Finally in step 210 a spatially dependent radiation attenuation coefficient is calculated. In step 210 this may include using the complete bone image, the fat-saturated image, the in-phase image, and/or the ultra-short echo time image.

Figure 3:
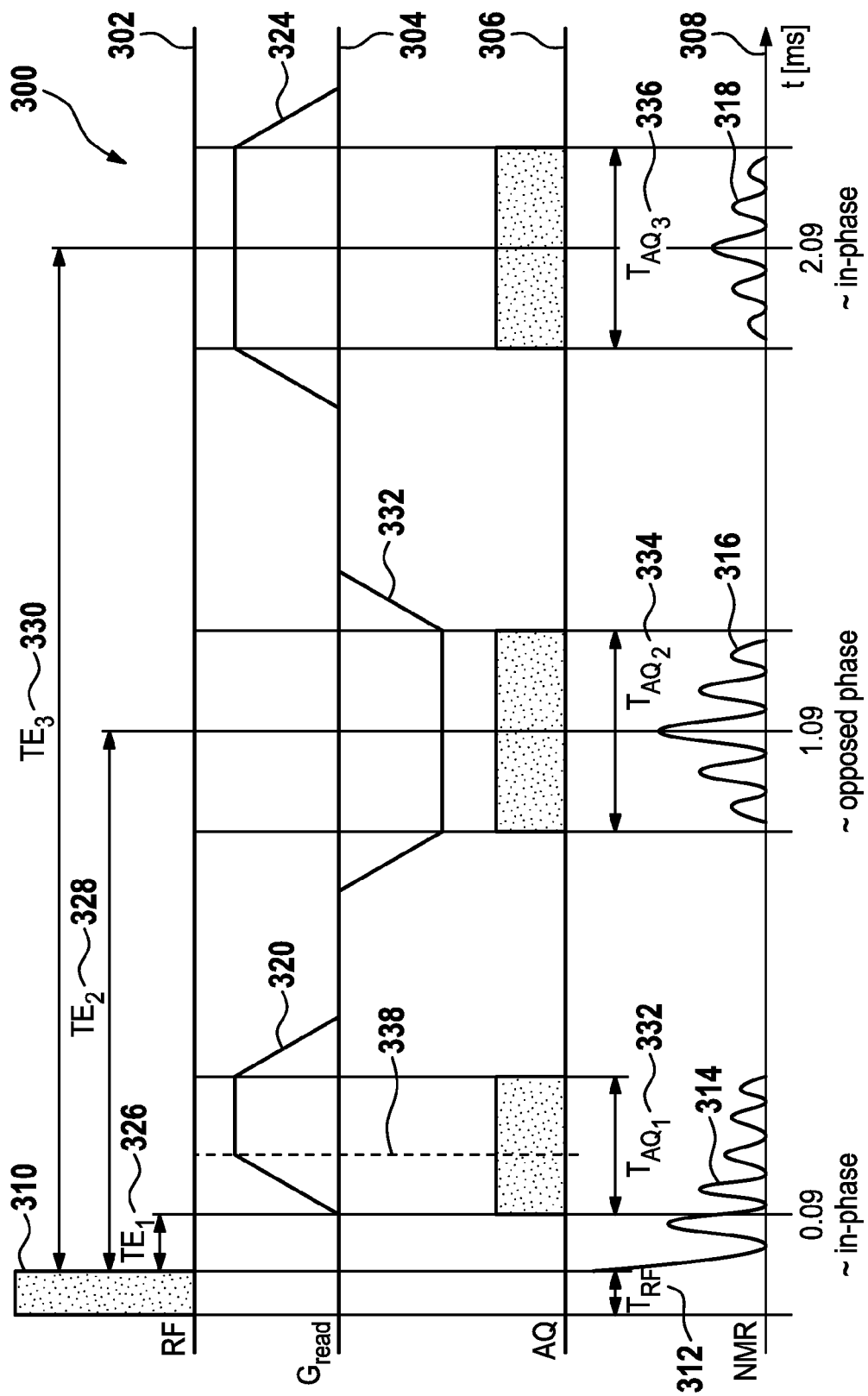
FIG. 3 illustrates a pulse sequence according to an embodiment of the invention in the form of a timing diagram.

FIG. 3 illustrates a pulse sequence 300 in the form of a timing diagram. In this pulse sequence 300 there are four timelines, there is timeline 302 which illustrates when radio frequency energy is applied. Timeline 304 illustrates the readout gradient. Timeline 306 illustrates a gate for data acquisition. Timeline 308 illustrates the nuclear magnetic resonance signal. On timeline 302 a radio frequency pulse 310 is applied during time Trf. On timeline 308 a free induction decay 314, a first gradient echo 316 and a second gradient echo 318 are shown. On timeline 308 there are three gradient pulses. Timeline 304 shows when a first gradient pulse 320, a second gradient pulse 322, and a third gradient pulse 324 are applied. The first gradient pulse 320 is applied during the free induction decay 314. The second gradient pulse 322 causes the first gradient echo 316. The third gradient pulse 324 causes the second gradient echo 318. The characteristic time rate at which the free induction decay 314 decays such as the T1, the T2, or T2* time constant is indicated as TE1 326. The first gradient echo 316 has a maximum at TE2 328. The second gradient echo 318 has a maximum at TE3 330.

Timeline 306 shows when magnetic resonance data is acquired. The free induction decay data is acquired during time interval Taq1 332. The first gradient echo data is acquired during time interval 334. The second gradient echo data is acquired during time interval 336. The pulse sequence illustrated in FIG. 3 is representative. Changes in the pulse sequence may be made. For instance the time when the free induction decay data is acquired may be delayed until the time marked 338.

In the example shown in FIG. 3, the echo times are chosen such that the echo times are acquired at in-phase and opposed-phase times. However, they do not need to be in-phase of opposed-phase echo times. An appropriate Dixon model may be used such that the gradient echoes may be acquired at non-specific echo time. For instance, various Dixon models will work for 2, 3, or 4 non-specific echo times.

Figure 4:
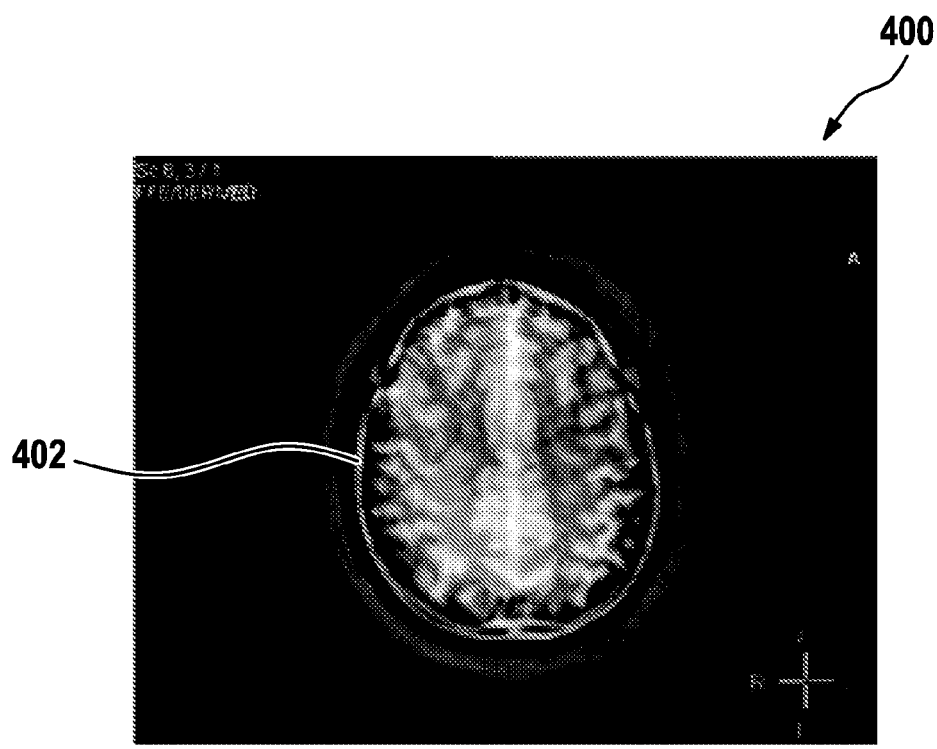
FIG. 4 shows a cortical bone image.

FIG. 4 shows an example of a cortical bone image 400. In this image 400 cortical bone 402 is shown. The cortical bone image 400 was constructed by subtracting the in-phase image from the ultra-short echo time image.

Figure 5:
FIG. 5 shows a medullary bone image.

FIG. 5 shows a medullary bone image. Medullary bone 502 is clearly shown in the medullary bone image 500.

Figure 6:
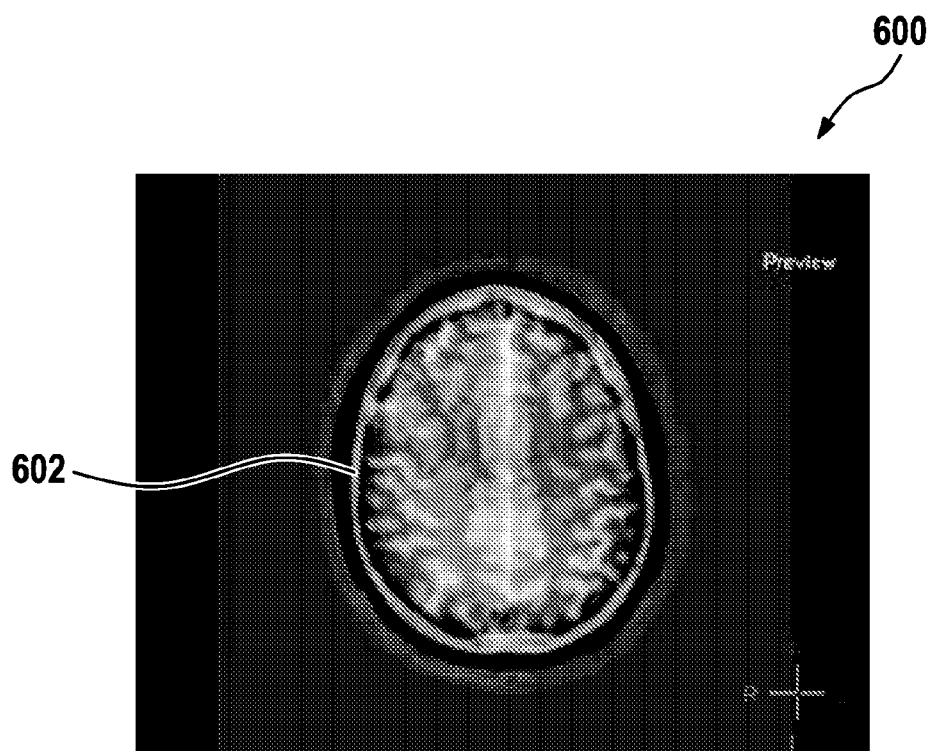
FIG. 6 shows a complete bone image.

FIG. 6 shows a complete bone image 600 that was constructed by adding images 400 and 500. In region 602 cortical plus medullary bone is shown.

Figure 7:
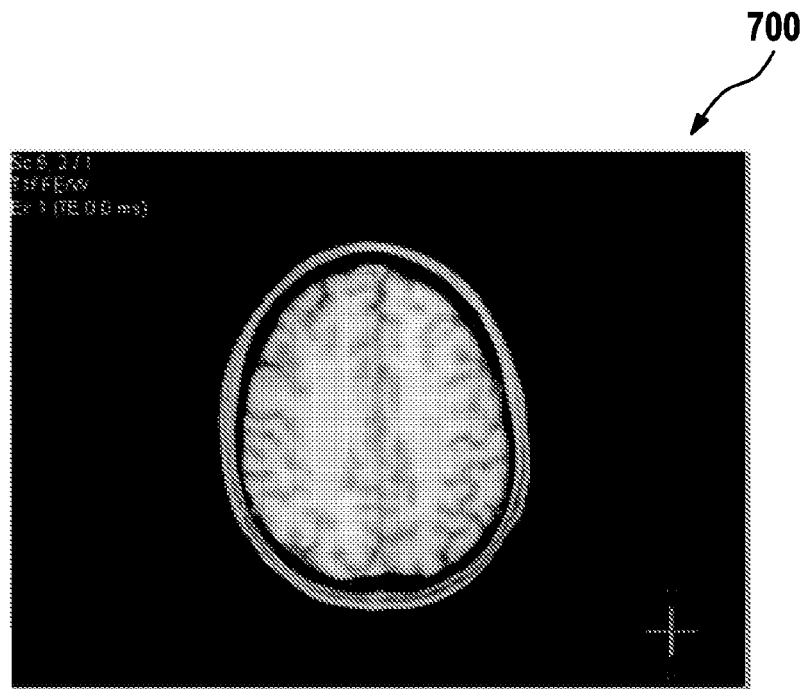
FIG. 7 shows a fat-saturated image.

FIG. 7 shows a fat-saturated image 700.

Figure 8:
FIG. 8 shows an in-phase image.

FIG. 8 shows an in-phase image 800.

Figure 9:
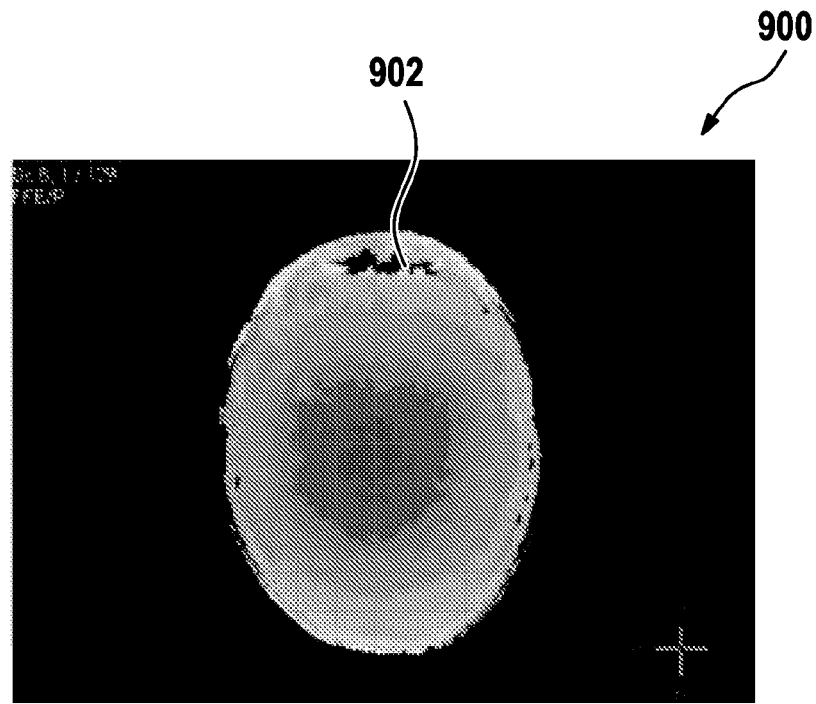
FIG. 9 shows the ultra-short echo time phase image.

FIG. 9 shows the ultra-short echo time image 900 for phase. An air cavity 902 is visible in this image.

Figure 10:
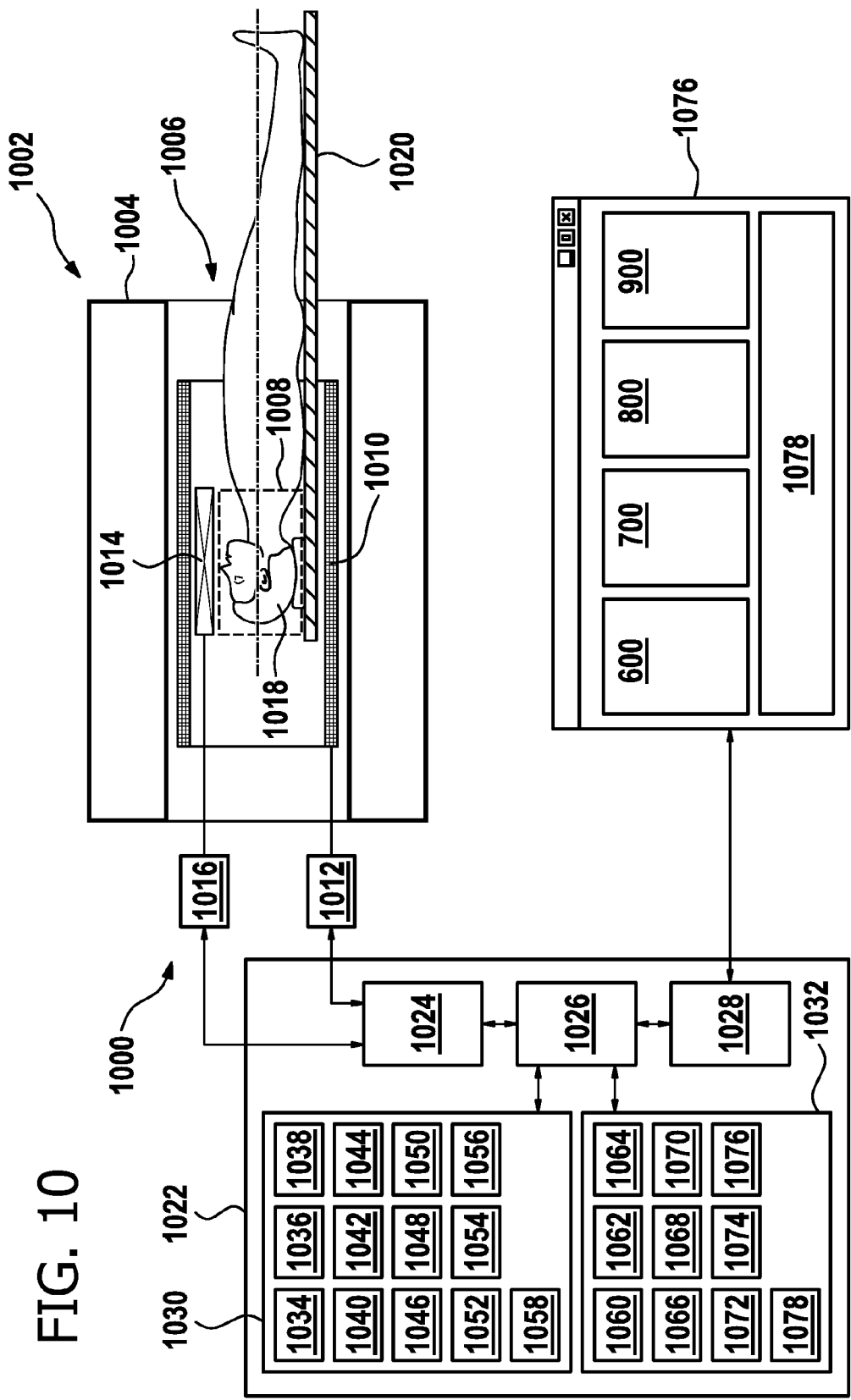
FIG. 10 shows a block diagram which illustrates a medical apparatus according to an embodiment of the invention.

FIG. 10 shows a block diagram which illustrates a medical apparatus 1000 according to an embodiment of the invention. The medical apparatus 1000 comprises a magnetic resonance imaging system 1002. The magnetic resonance imaging system 1002 is shown as comprising a magnet 1004. The magnet 1004 shown in FIG. 10 is a cylindrical type superconducting magnet. The magnet 1004 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 1006 of the cylindrical magnet 1004 there is an imaging zone 1008 where the magnetic field is strong and uniform enough to perform magnetic resonance imaging.

Within the bore 1006 of the magnet 1004 there is also a magnetic field gradient coil 1010 which is used for acquisition of magnetic resonance data to spatially encode magnetic spins within the imaging zone 1008 of the magnet 1004. The magnetic field gradient coil 1010 is connected to a magnetic field gradient coil power supply 1012. The magnetic field gradient coil 1010 is intended to be representative. Typically magnetic field gradient coils 1010 contain three separate sets of coils for spatially encoding in three orthogonal spatial directions. A magnetic field gradient power supply supplies current to the magnetic field gradient coils. The current supplied to the magnetic field coils is controlled as a function of time and may be ramped or pulsed.

Adjacent to the imaging zone 1008 is a radio frequency coil 1014 for manipulating the orientations of magnetic spins within the imaging zone 1008 and for receiving radio transmissions from spins also within the imaging zone 1008. The radio frequency coil may contain multiple coil elements. The radio frequency coil or each of any multiple coil elements may also be referred to as a channel. The radio frequency coil may also be referred to as an antenna. The radio frequency coil 1014 is connected to a radio frequency transceiver 1016. The radio frequency coil 1014 and radio frequency transceiver 1016 may be replaced by separate transmit and receive coils and a separate transmitter and receiver. It is understood that the radio frequency coil 1014 and the radio frequency transceiver 1016 are representative. The radio frequency coil 1014 is intended to also represent a dedicated transmit antenna and a dedicated receive antenna. Likewise the transceiver 1016 may also represent a separate transmitter and receivers.

The transceiver 1016 and the magnetic field gradient coil power supply 1012 are connected to a hardware interface 1024 of a computer system 1022. The computer system 1022 further comprises a processor 1026. The processor is connected to the hardware interface 1024 which enables the processor 1026 to control the operation and function of the medical apparatus 1000. The processor 1026 is further connected to user interface 1028. The processor 1026 is also connected to computer storage 1030 and computer memory 1032.

The computer storage 1030 is shown as containing a pulse sequence 1034. The pulse sequence 1034 may be used for controlling the magnetic resonance imaging system 1002. The computer storage 1030 is shown as further containing magnetic resonance data 1036 that was acquired from the magnetic resonance imaging system 1002 using the pulse sequence 1034. The computer storage 1030 is further shown as containing an in-phase image 1038, a fat-saturated image 1040, a water-saturated image 1042 and an ultra-short echo time image 1044 that was reconstructed from the magnetic resonance data 1036. The computer storage 1030 is also shown as containing an opposed phase image 1046 that was reconstructed from the magnetic resonance data 1036. The opposed phase image 1046 is not calculated or reconstructed in all embodiments.

The computer storage 1030 is further shown as containing a medullary bone image reconstructed from the water-saturated image 1042. The computer storage 1030 is further shown as containing a cortical bone image 1050 reconstructed by subtracting the in-phase image 1038 from the ultra-short echo time image 1044. The computer storage 1030 is shown as further containing a complete bone image 1052 which is constructed by adding the medullary bone image 1048 to the cortical bone image 1050. The computer storage 1030 is shown as containing a spatially dependent radiation attenuation coefficient 1054 which is not present in all embodiments. The computer storage 1030 is further shown as containing a radiation therapy planning data 1056. The radiation therapy planning data 1056 is optional and is not present in all embodiments. The computer storage 1030 is further shown as containing a treatment plan 1058 which is optional also.

The computer memory 1032 contains computer executable instructions for controlling the operation and functioning of the medical apparatus 1000. The computer memory 1032 is shown as containing a control module 1060. The control module 1060 contains computer executable code which allows the processor 1026 to control the operation and function of the medical apparatus 1000. The computer storage 1032 is further shown as containing an image reconstruction module 1062. The image reconstruction module 1062 contains computer executable code for reconstructing the images 1038, 1040, 1042, 1044, 1046 contained within the computer storage 1030. The computer memory 1032 further contains an image manipulation module 1064 which allows the processor 1026 to manipulate such as adding and subtracting images.

The computer memory 1032 is shown as optionally containing a three-point Dixon signal model which may be used by the image reconstruction module 1062. The computer memory 1032 is further shown as containing an image segmentation module 1068. In some embodiments the image segmentation module may be used to segment any of the images contained within the computer storage 1030. The computer memory 1032 is further shown as containing the radiation attenuation coefficient calculation module 1070. The radiation attenuation coefficient calculation module 1070 may in some embodiments be used to calculate the spatially dependent radiation attenuation coefficient 1054 from the complete bone image 1052, the fat-saturated image 1040, the in-phase image 1038, and the ultra-short echo time image 1044.

In some embodiments there may be a radiation therapy planning data generation module 1072 present in the computer memory 1032. The radiation therapy planning generation module 1072 is adapted for automatically generating the radiation therapy planning data 1056 using the treatment plan 1058 and the spatially dependent radiation attenuation coefficient 1054. Some embodiments may also have a graphical user interface control module 1074 present in the computer memory 1032 for controlling the operation and function of a graphical user interface 1076. The optional graphical user interface 1076 is shown as displaying a complete bone image 600, a fat-saturated image 700, an in-phase image 800, and an ultra-short echo time image 900. The graphical user interface 1076 further contains a radiation therapy planning interface 1078 where an operator or physician may enter radiation therapy planning data 1056.

Figure 11:
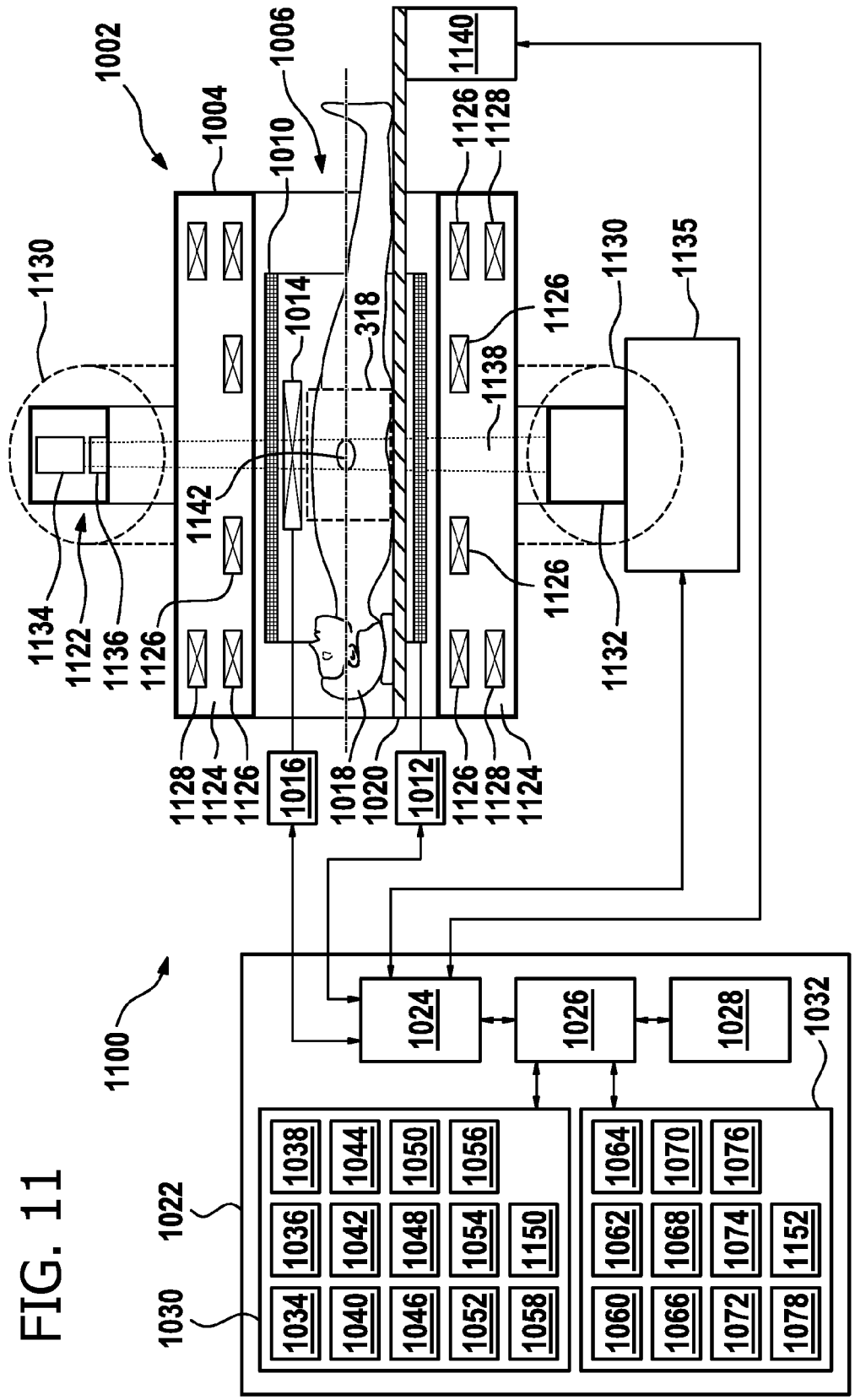
FIG. 11 shows a block diagram which illustrates a medical apparatus according to a further embodiment of the invention.

FIG. 11 shows an embodiment similar to that shown in FIG. 10. The medical apparatus shown in FIG. 11 includes a radiation therapy system 1122. The magnet 1004 is a superconducting magnet and includes a cryostat 1124 with several superconducting coils 1126. There is also a compensation coil 1128 which creates an area of reduced magnetic field 1130 which surrounds the magnet 1004. The radiation therapy system 1122 in this embodiment is intended to be representative of radiation therapy systems in general. The components shown here are typical for LINAC and x-ray therapy systems. However with minor modifications such as using a split magnet charged particles or beta particle radiation therapy systems can also be illustrated using this diagram. There is a gantry 1132 which is used to rotate a radiotherapy source 1134 about the magnet 1004. The gantry 1132 is rotated about the axis of rotation 1133 by a rotation actuator 1135. There is a radiation therapy source 1134 which is rotated by the gantry 1132. The radiotherapy source 1134 generates a radiation beam 1138 which passes through collimator 1136. In the Fig. a target zone labeled 1142 which is irradiated by the radiation beam 1138 is shown. As the radiation source 1134 rotates about the axis of rotation 1133 the target zone 1142 is irradiated. There is also a support positioning system 1140 for positioning the support 1020 to optimize the location of the target zone 1142 relative to the radiation therapy system 1122.

The hardware interface 1024 is shown as being connected to the transceiver 1016, the power supply 1012, the rotation actuator 1135, and the support positioning system 1140. The hardware interface 1024 allows the processor 1026 to send and receive control signals to all of these components 1012, 1016, 1135, 1140.

The computer storage 1030 is shown as containing radiation therapy control commands 1150. The radiation therapy control commands 1150 comprise instructions that when executed by the radiation therapy system 1122 cause the radiation therapy system 1122 to treat the target zone 1142. The computer memory 1032 is shown as containing a radiation therapy control command generation module 1152. The radiation therapy control command generation module 1152 contains instructions which allow the processor 1026 to generate the radiation therapy control commands 1150 from the radiation therapy planning data 1056.

Figure 12:
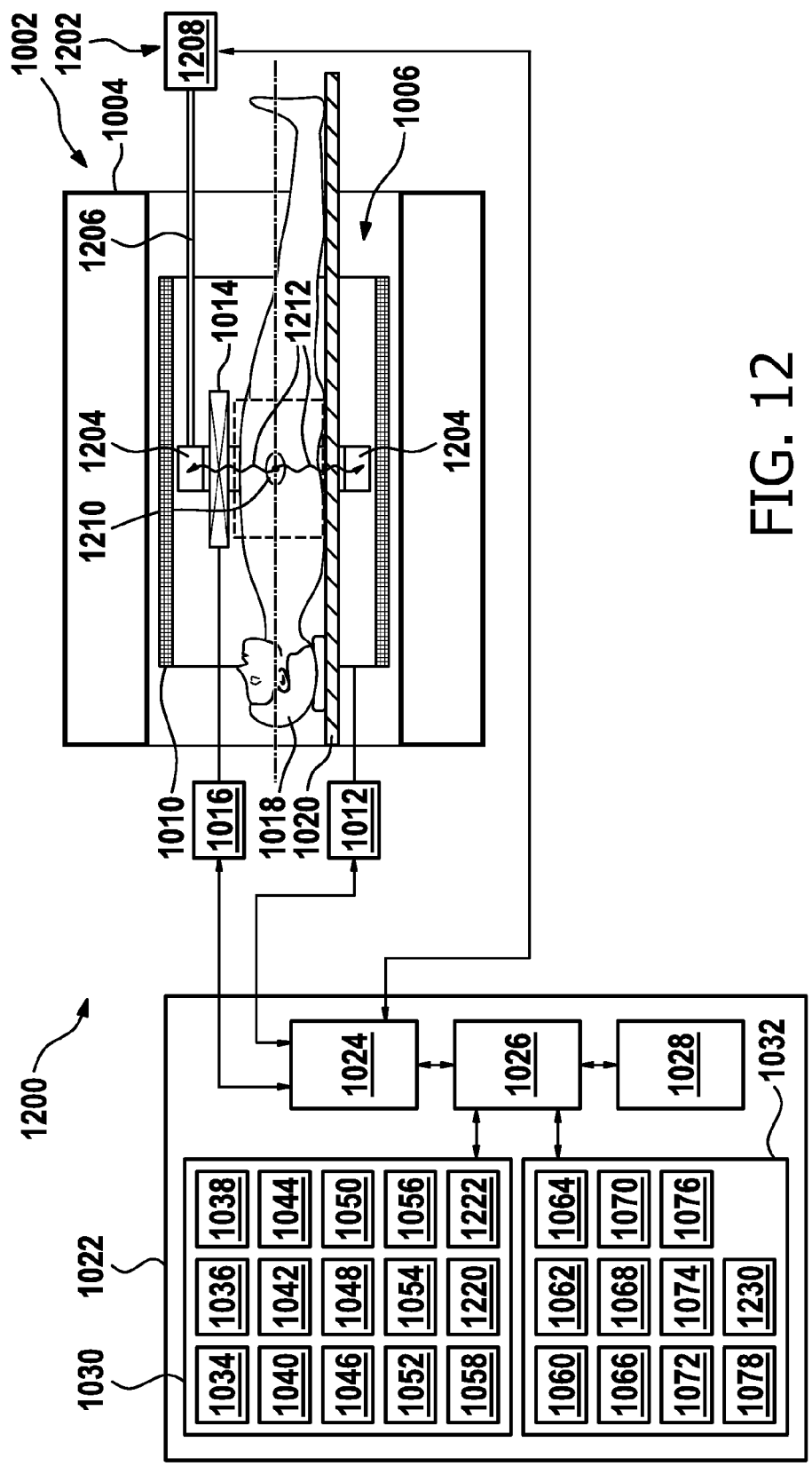
FIG. 12 shows a block diagram which illustrates a medical apparatus according to a further embodiment of the invention.

FIG. 12 illustrates a medical apparatus 1200 similar to that shown in FIG. 10. In this embodiment a radio isotope imaging system 1202 has been integrated into the medical apparatus 1200. The radio-isotope imaging system 1202 comprises a scintillator ring 1204 adapted for detecting ionizing radiation. The individual scintillators which make up the scintillator ring may be connected to a set of light pipes 1206 or fiber optics which are led out of the magnet 1004 to a series of light detectors 1208. Within the subject 1018 is shown a concentration of radio-isotope 1210. Ionizing radiation is emitted 1212 and is absorbed in the scintillator ring 1204. Within the computer storage 1030 is shown the radio-isotope imaging data 1220. The radio-isotope imaging data 1220 is the recorded data acquired by the light detectors 1208. The computer storage 1030 is further shown as containing a medical image 1222. The medical image is an image, reconstruction, or rendering of the radio-isotope imaging data which is descriptive of the location of radio-isotope 1210 within the subject.

The medical image 1222 was reconstructed from the radio-isotope imaging data 1220. The radio-isotope imaging system 1202 may for instance be a positron emission tomography system or a single photon emission computer tomography system. The computer memory 1032 is shown as containing a medical image reconstruction module 1230. The medical image reconstruction module 1230 contains computer executable code which the processor 1026 may use to reconstruct the medical image 1222 from the radio-isotope imaging data 1220. The computers 1022 shown in the embodiments of FIGS. 10, 11, and 12 are equivalent as is the software and data stored within the computer memory 1032 and computer storage 1030 respectively.

Figure 13:
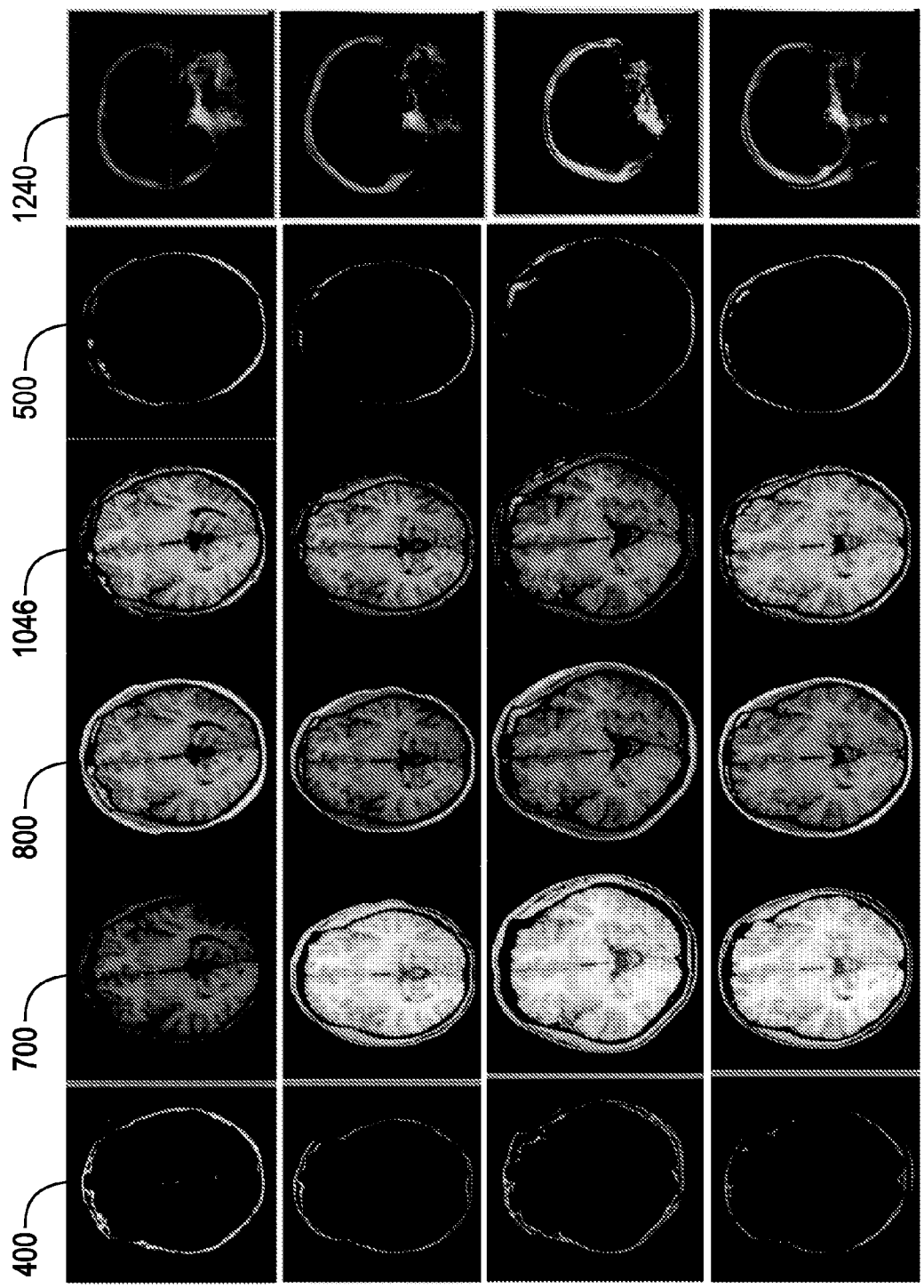
FIG. 13 shows images for four subjects which include Digital Reconstructed Radiographs (DRRs).

FIG. 13 shows images for four subjects. Each row includes images for one subject generated by the single imaging sequence. The columns of images from left to right include bone-enhanced images 400, water-only images 700, in-phase images 800, opposed-phase images 1046, fat-only images 500, and digital reconstructed radiographs (DRRs)

1240. The bone enhanced images 400 contrast cortical bone corresponding to FIG. 4 and are constructed by subtracting the in-phase image 800 from the ultra-short echo time image corresponding to FIG. 9. The difference between the images of FIG. 4 and the column of bone enhanced images includes a weighting of the in-phase image which reduces the presence of the brain. The water-only images 700 are T1w images with fat-saturation corresponding to FIG. 7. The in-phase images 800 correspond to FIG. 8. The fat-only images 500 correspond to FIG. 5 and include medullary bone. The last column includes the DRRs 1240. The DRR is constructed as a 2-dimensional projection of the 3-dimensional volume of the bone-enhance image 400. Alternatively, the DRR is constructed as a 2-dimensional projection of the weighted in-phase image subtracted from the ultra-short echo time image. The projections are shown as sagittal perspectives. The DRRs are of sufficient quality to be used in 2-dimensional patient matching. Patient matching is used to position the subject 1018 in radiation therapy. Adjustments to the subject 1018 position are done by the support positioning system 1140. The DRR images can replace conventional CT images.

In another embodiment, the bone enhanced image or cortical bone image are used to register the images with other images including other imaging modalities such as PET, SPECT, CT, etc. The images generated from the pulse sequence 300 are inherently registered. The bone-enhanced images provide both registration and density information for attenuation. Furthermore, the generated MR images from the pulse sequence include soft-tissue images which further enhance attenuation.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 pulse sequence
302 RF
304 read out gradient
306 data acquisition gate
308 nuclear magnetic resonance signal
310 radio frequency pulse
312 time $T_{RF}$
314 free induction decay
316 first gradient echo
318 second gradient echo
320 first gradient pulse
322 second gradient pulse
324 third gradient pulse
326 $TE_1$
328 $TE_2$
330 $TE_3$
332 TAQ1
334 TAQ2
336 TAQ3
400 cortical bone image
402 cortical bone
500 medullary bone image
502 medullary bone
600 complete bone image
602 cortical plus medullary bone
700 fat-saturated image
800 in-phase image
900 ultra-short echo time image (phase)
902 air
1000 medical apparatus
1002 magnetic resonance imaging system
1004 magnet
1006 bore of magnet
1008 imaging zone
1010 magnetic field gradient coil
1012 magnetic field gradient coil power supply
1014 radio frequency coil
1016 transceiver
1018 subject
1020 subject support
1022 computer
1024 hardware interface
1026 processor
1028 user interface
1030 computer storage
1032 computer memory
1034 pulse sequence
1036 magnetic resonance data
1038 in-phase image
1040 fat-saturated image
1042 water-saturated image
1044 ultra-short echo time image
1046 opposed phase image
1048 medullary bone image
1050 cortical bone image
1052 complete bone image
1054 spatially dependent radiation attenuation coefficient
1056 radiation therapy planning data
1058 treatment plan
1060 control module
1062 image reconstruction module
1064 image manipulation module
1066 three-point Dixon signal model
1068 image segmentation module
1070 radiation attenuation coefficient calculation module
1072 radiation therapy planning data generation module
1074 graphical user interface control module
1076 graphical user interface
1078 radiation therapy planning interface
1122 radiation therapy system
1124 cryostat
1126 superconducting coil
1128 compensation coil
1130 reduced magnetic field region
1132 gantry
1133 axis of rotation
1134 radiotherapy source 1135 rotational actuator
1138 radiation beam
1140 support positioning system
1142 target zone
1150 radiation therapy control commands
1152 radiation therapy control command generation module
1200 medical apparatus
1202 radio-isotope imaging system
1204 scintillator ring
1206 light pipes
1208 light detectors
1210 concentration of radio isotope
1212 radiation
1220 radio-isotope imaging data
1222 medical image
1230 medical image reconstruction module
1240 digital reconstructed radiograph (DRR)

The invention claimed is:

1. A medical apparatus comprising:
a magnetic resonance imaging system which acquires magnetic resonance data from an imaging volume;
a processor for controlling the medical apparatus; and
a memory containing machine executable instructions and a pulse sequence for a single acquisition, wherein the magnetic resonance data acquired using the pulse sequence comprises free induction decay data and multiple gradient echo data, wherein execution of the instructions causes the processor to:
acquire the magnetic resonance data using the magnetic resonance imaging system in accordance with the pulse sequence in a single acquisition; and
reconstruct an in-phase image comprising an image with fat and water signals in phase, a fat-saturated image, a water-saturated image, and an ultra-short echo time image from the magnetic resonance data acquired in the single acquisition, wherein the ultra-short echo time image comprises bone image data,
construct a medullary bone image from the water-saturated image;
construct a cortical bone image by subtracting the in-phase image from the ultra-short echo time image;
construct a complete bone image by adding the medullary bone image to the cortical bone image, and
calculate a spatially dependent radiation attenuation coefficient using anatomical information retrieved from the complete bone image, the fat-saturated image, the in-phase image, and the ultra-short echo time image.

2. The medical apparatus of claim 1, wherein the ultra-short echo time image is used for differentiating bone and air, wherein the in-phase image is used for image segmentation, and wherein the fat saturated image is used for image segmentation.

3. The medical apparatus of claim 2, wherein further execution of the instructions causes the processor to:
display the fat-saturated image, the in-phase image, the complete bone image and the ultra-short echo time image on a graphical user interface; and
receive radiation therapy planning data from the graphical user interface.

4. The medical apparatus of claim 1, wherein execution of the instructions further causes the processor to generate radiation therapy planning data using the fat-saturated image, the in-phase image, the ultra-short echo time image, the complete bone image, the spatially dependent radiation attenuation coefficient, and a treatment plan with a radiation therapy planning program module.

5. The medical apparatus of claim 4, wherein the medical apparatus further comprises a radiation therapy system, wherein the execution of the instructions further causes the processor to:
generate radiation therapy control commands using the radiation therapy planning data; and
treat the subject with the radiation therapy system by executing the radiation therapy control commands.

6. The medical apparatus of claim 5, wherein the radiation therapy system is any one of the following: a linear accelerator, a gamma knife, a charged particle therapy system, a proton therapy system, an x-ray therapy system, external beam radiation system, and a brachytherapy system.

7. The medical apparatus of claim 1, wherein execution of the instructions further causes the processor to:
receive radio-isotope imaging data, and
calculate a medical image using the radio-isotope image data and the spatially dependent radiation attenuation coefficient.

8. The medical apparatus of claim 7, wherein the medical apparatus further comprises a radio-isotope imaging system for acquiring the radio-isotope imaging data, wherein the radio-isotope imaging system is any one of the following: a positron emission tomography system and a single photon emission computed tomography system, and wherein execution of the instructions further causes the processor to acquire the radio-isotope imaging data using the radio-isotope imaging system.

9. The medical apparatus of claim 1, wherein execution of the instructions further causes the processor to reconstruct an opposed phase image comprising an image with fat and water signals 180 degrees out of phase from the magnetic resonance data.

10. The medical apparatus of claim 1, wherein execution of the instructions further causes the processor to reconstruct multiple echo images, wherein the in-phase image, the fat-saturated image, the water-saturated image, and the ultra-short echo time image are reconstructed from the multiple echo images using a Dixon signal model.

11. The medical apparatus of claim 1, wherein execution of the instructions further causes the processor to construct a digital reconstructed radiograph image based on the cortical bone image.

12. The medical apparatus of claim 11, wherein the digital reconstructed radiograph image is used for 2-dimensional patient matching with a support positioning system.

13. A method of operating a medical apparatus, wherein the medical apparatus comprises a magnetic resonance imaging system for acquiring magnetic resonance data from an imaging volume, wherein the method comprises the steps of:
acquiring the magnetic resonance data in a single acquisition using the magnetic resonance imaging system, wherein the magnetic resonance data acquired in the single acquisition comprises free induction decay data and multiple gradient echo data; and
reconstructing an in-phase image comprising an image with fat and water signals in phase, a fat-saturated image, a water-saturated image, and an ultra-short echo time image from the magnetic resonance data acquired in the single acquisition, wherein the ultra-short echo time image comprises bone image data;
constructing a medullary bone image from the water-saturated image;

constructing a cortical bone image by subtracting the in-phase image from the ultra-short echo time image;

constructing a complete bone image by adding the medullary bone image to the cortical bone image;

performing image segmentation to differentiate at least regions of cortical bone, medullary bone, fat, and air;

calculating a spatially dependent radiation attenuation coefficient using at least anatomical information retrieved from the image segmentation.

14. The method according to claim 13, further including:

constructing a digital reconstructed radiograph image based on a 2-dimensional projection of the ultra-short echo time image.

15. The method according to claim 14, further including:

matching a patient position with a support positioning system in a radiation therapy system in 2-dimensions based on the digital reconstructed radiograph image.

16. The method according to claim 13, wherein the cortical bone image is used to register the images.

17. A non-transitory computer-readable storage medium containing machine readable instructions for execution by a processor controlling a medical apparatus, wherein the medical apparatus comprises a magnetic resonance imaging system for acquiring magnetic resonance data from an imaging volume, wherein the computer-readable storage medium further contains a pulse sequence for controlling the magnetic resonance imaging system, wherein the magnetic resonance data acquired using the pulse sequence comprises free induction decay data and multiple gradient echo data, wherein execution of the instructions causes the processor to:

acquire the magnetic resonance data using the magnetic resonance imaging system; and reconstruct an in-phase image comprising an image with fat and water signals in phase, a fat-saturated image, a water-saturated image, and an ultra-short echo time image from the magnetic resonance data, wherein the ultra-short echo time image comprises bone image data;

constructing a medullary bone image from the water-saturated image;

constructing a cortical bone image by subtracting the in-phase image from the ultra-short echo time image; and constructing a complete bone image by adding the medullary bone image to the cortical bone image calculating a spatially dependent radiation attenuation coefficient using anatomical information retrieved from the complete bone image, the fat-saturated image, the in-phase image, and the ultra-short echo time image.

18. A controller for a medical apparatus, wherein the medical apparatus comprises a magnetic resonance imaging system for acquiring magnetic resonance data from an imaging volume; wherein the controller is configured to:

acquire the magnetic resonance data using the magnetic resonance imaging system, wherein the controller is arranged to use a pulse sequence to control the operating of the magnetic resonance imaging system during acquisition of the magnetic resonance data, wherein the magnetic resonance data acquired using the pulse sequence comprises free induction decay data and multiple gradient echo data; and reconstruct at least an in-phase image comprising an image with fat and water signals in phase, a water-saturated image, and an ultra-short echo time image from the magnetic resonance data, wherein the ultra-short echo time image comprises bone image data;

constructing a medullary bone image from the water-saturated image;

constructing a cortical bone image by subtracting the in-phase image from the ultra-short echo time image; and constructing a complete bone image by adding the medullary bone image to the cortical bone image calculating a spatially dependent radiation attenuation coefficient using anatomical information retrieved from at least the complete bone image, the in-phase image, and the ultra-short echo time image.

* * * * *